United States Patent [19]
Sakaki et al.

[11] Patent Number: 5,698,492
[45] Date of Patent: Dec. 16, 1997

[54] HERBICIDAL COMPOSITION CONTAINING 2-(4-CHLORO-2-FLUORO-5-(N-PENTYLOXY CARBONYLMETHOXY)-4,5,6,7-TETRAHYDRO-2H-ISOINDOLE-1,3-DIONE

[75] Inventors: Masaharu Sakaki; Kazuo Saitoh, both of Osaka, Japan

[73] Assignee: Sumitomo Chemical Company, Limited, Osaka, Japan

[21] Appl. No.: 958,695

[22] Filed: Oct. 9, 1992

[30] Foreign Application Priority Data

Oct. 16, 1991 [JP] Japan .................. 3-267493

[51] Int. Cl.$^6$ .................. H01N 43/38; H01N 57/04
[52] U.S. Cl. .................. 504/128; 504/205; 504/206; 504/204; 504/286
[58] Field of Search .................. 71/96, 86; 504/204, 504/205, 206, 286, 128

[56] References Cited

U.S. PATENT DOCUMENTS

| | | | |
|---|---|---|---|
| 3,799,758 | 3/1974 | Franz | 71/86 |
| 4,168,963 | 9/1979 | Rupp et al. | 71/86 |
| 4,670,046 | 6/1987 | Nagano et al. | 71/96 |
| 4,756,743 | 7/1988 | Morita et al. | 71/92 |
| 4,770,695 | 9/1988 | Nagano et al. | 71/96 |
| 4,906,289 | 3/1990 | Yoshida et al. | 71/96 |
| 4,935,050 | 6/1990 | Morita et al. | 71/94 |
| 4,938,795 | 7/1990 | Nagano et al. | 71/96 |
| 4,994,102 | 2/1991 | Yoshido et al. | 71/86 |
| 5,108,488 | 4/1992 | Etheridge | 71/98 |

FOREIGN PATENT DOCUMENTS

| | | |
|---|---|---|
| 0083055 | 12/1982 | European Pat. Off. . |
| 0181628 | 11/1985 | European Pat. Off. . |
| 0204146 | 4/1986 | European Pat. Off. . |
| 0232504 | 12/1986 | European Pat. Off. . |
| 0352508 | 7/1989 | European Pat. Off. . |
| 0354346 | 7/1989 | European Pat. Off. . |
| A142409 | 10/1987 | Japan . |

OTHER PUBLICATIONS

The Pesticide Manual p. 449–450, *Glyphosate*. 1991.
*Zyosozai Kenkyu Soran*, Herbicide Studies Handbook, pp. 611–612 1990.
The Pesticide Manual p. 448, *Glufosinate* 1991.

*Primary Examiner*—S. Mark Clardy
*Assistant Examiner*—B. Bembenick
*Attorney, Agent, or Firm*—Birch, Stewart, Kolasch & Birch, LLP

[57] ABSTRACT

There is disclosed a herbicidal composition containing (a) 2-[4-chloro-2-fluoro-5-(n-pentyloxycarbonylmethoxy)phenyl]-4,5,6,7-tetrahydro-2H-isoindole-1,3-dione and (b) at least one selected from the group consisting of N-(phosphonomethyl)glycine, (2-amino-4-methylphosphinobutyryl)alanylalanine, DL-homoalanin-4-yl(methyl)phosphinic acid and salts thereof. Also disclosed is a method for controlling undesired weeds by application of the herbicidal composition.

24 Claims, No Drawings

HERBICIDAL COMPOSITION CONTAINING 2-(4-CHLORO-2-FLUORO-5-(N-PENTYLOXY CARBONYLMETHOXY)-4,5,6,7-TETRAHYDRO-2H-ISOINDOLE-1,3-DIONE

FIELD OF THE INVENTION

The present invention relates to a herbicidal composition, and more particularly, to a herbicidal composition which is a combination of particular active ingredients.

BACKGROUND OF THE INVENTION

In recent years, a number of herbicides have been used for weeding in agricultural and non-agricultural fields. There is, however, many kinds of weeds to be exterminated or controlled, and it is desired to develop excellent herbicides having a stronger herbicidal activity against a wide variety of weeds, i.e., having a wider weeding spectrum.

Many of the herbicides are applied to agricultural fields before plowing or planting of crops. In that case, it is desired to use herbicides that exert herbicidal effect rapidly because it becomes possible to plow or plant crops earlier in these agricultural fields after the treatment. Such a herbicide is further required to have no material phytotoxicity against the planted crops after the treatment.

SUMMARY OF THE INVENTION

Under these circumstances, the present inventors have intensively studied various herbicidal compounds, and found that a combination of particular herbicidal compounds as active ingredients is useful for herbicidal compositions having an excellent herbicidal activity.

According to the present invention, there is provided a herbicidal composition comprising as active ingredients a herbicidally effective amount of (a) 2-[4-chloro-2-fluoro-5-(n-pentyloxycarbonylmethoxy)phenyl]-4,5,6,7-tetrahydro-2H-isoindole-1,3-dione of the formula:

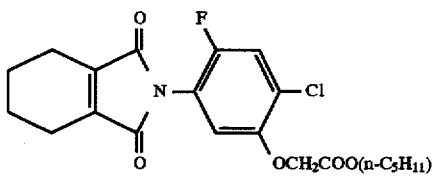

and (b) at least one selected from the group consisting of N-(phosphonomethyl)glycine of the formula:

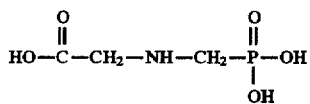

and salts thereof, (2-amino-4-methylphosphinobutyryl) alanylalanine of the formula:

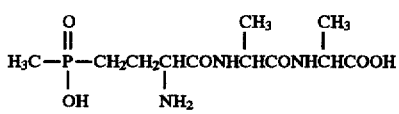

and salts thereof, DL-homoalanin-4-yl(methyl)phosphinic acid of the formula:

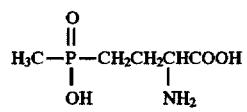

and salts thereof.

The present invention also provides a method for controlling undesired weeds, which comprises applying the above herbicidal composition to the area where undesired weeds grow.

DETAILED DESCRIPTION OF THE INVENTION

The herbicidal composition of the present invention is characterized by the combined use of active ingredients (a) and (b). This combined use provides the excellent advantages of exterminating or controlling a wide variety of weeds in agricultural and non-agricultural fields, and rapidly exerting a herbicidal effect in comparison with the sole use of each of these ingredients, viz., the rapidity of a herbicidal effect is enhanced synergistically, thereby making it possible to apply the composition at a smaller dosage which is favorable from the economical point of view. Moreover, the herbicidal composition of the present invention has substantially no material phytotoxicity against the planted crops after the treatment therewith.

The herbicidal composition of the present invention can exterminate or control a wide variety of weeds, examples of which are broad-leaf weeds such as wild buckwheat (*Polygonum convolvulus*), pale smartweed (*Polygonum lapathifolium*), curly dock (*Rumex crispus*), common purslane (*Portulaca oleracea*), common chickweed (*Stellaria media*), water chickweed (*Stellaria aquatica*), common lambsquarters (*Chenopodium album*), redroot pigweed (*Amaranthus retroflexus*), wild mustard (*Sinapis arvensis*), shepherdspurse (*Capsella bursa-pastoris*), hemp sesbania (*Sesbania exaltata*), sicklepod (*Cassia obtusifolia*), Japanese hedgeparsley (*Torilis japonica*), velvetleaf (*Abutilon theophrasti*), prickly sida (*Sida spinosa*), field pansy (*Viola arvensis*), catchweed bedstraw (*Galium aparine*), ivyleaf morningglory (*Ipomoea hederacea*), tall morningglory (*Ipomoea purpurea*), field bindweed (*Convolvulus arvensis*), red deadnettle (*Lamium purpureum*), henbit (*Lamium amplexicaure*), jimsonweed (*Datura stramonium*), black nightshade (*Solanum nigrum*), persian speedwell (*Veronica persica*), common cocklebur (*Xanthium pensylvanicum*), common sunflower (*Helianthus annus*), scentless chamomile (*Matricaria perforata*), corn marigold (*Chrysanthemum segetum*), Japanese mugwort (*Artemisia princeps*), tall goldenrod (*Solidago altissima*) and corn spurry (*Spergula arvensis*); gramineous weeds such as colorado bluestem (*Agropyron tsukushiense*), barnyardgrass (*Echinochloa crusgalli*), green foxtail (*Setaria viridis*), giant foxtail (*Setaria faberi*), large crabgrass (*Digitaria sanguinalis*), annual bluegrass (*Poa annua*), blackgrass (*Alopecurus myosuroides*), oats (*Avena sativa*), wild oats (*Avena fatua*), johnsongrass (*Sorghum halepense*), quackgrass (*Agropyron repens*), downy brome (*Bromus tectorum*) and bermudagrass (*Cynodon dactylon*); commelinaceous weeds such as Asiatic dayflower (*Commelina communis*); and cyperaceous weeds such as rice flatsedge (*Cyperus iria*) and purple nutsedge (*Cyperus rotundus*).

In cases where the herbicidal composition of the present invention is applied to agricultural fields before plowing or planting of crops, it should be noted that the herbicidal composition of the present invention has substantially no phytotoxicity against main crops such as soybean (*Glycine max*), corn (*Zea mays*), cotton (*Gossupium hirsutum*), wheat (*Triticum aestivum*), sugar beet (*Beta vulgaris*), barley (*Hordeum vulgare*) and rice (*Oryza sativa*); and vegetables such as radish (*Raphanus sativus*), onion (*Allium cepa*) and carrot (*Daucus carota* var. *sativus*).

The active ingredients (a) and (b) are already known in the art; for example, 2-[4-chloro-2-fluoro-5-(n-pentyloxycarbonylmethoxy)phenyl]-4,5,6,7-tetrahydro-2H-isoindole-1,3-dione is disclosed in the specification of U.S. Pat. No. 4,670,046; N-(phosphonomethyl)glycine and salts thereof (hereinafter referred to as glyphosate) are herbicides described by C. R. Worthing et al., in "The Pesticide Manual", 8th ed., 1987, pp. 449–450; (2-amino-4-methylphosphinobutyryl)alanylalanine and salts thereof (hereinafter referred to as bialaphos) are herbicides described by Tetsuo Takematsu, in "Josoh-zai Kenkyu Sohran (General Survey of Herbicide Research)", 1982, p. 611; and DL-homoalanin-4-yl(methyl)phosphinic acid and salts thereof (hereinafter referred to as glufosinate) are herbicides described by C. R. Worthing et al., in "The Pesticide Manual", 8th ed., 1987, p. 448.

Examples of the salts of N-(phosphonomethyl)glycine are pesticidally acceptable salts such as isopropylamine salts, ammonium salts and trimethylsulfonium salts. Examples of the salts of (2-amino-4-methylphosphinobutyryl)alanylalanine are pesticidally acceptable salts such as sodium salts. Examples of the salts of DL-homoalanin-4-yl (methyl)phosphinic acid are pesticidally acceptable salts such as ammonium salts.

The weight ratio of ingredients (a) to (b) is usually 1:0.25 to 100, preferably 1:0.5 to 70, although it may vary in a considerably wide range.

For the practical usage of the herbicidal composition of the present invention, it is usually formulated by independently mixing each of the active ingredients with conventional solid or liquid carriers, surfactants and other adjuvants to form conventional formulations such as wettable powders, flowables, water-dispersible granules, emulsifiable concentrates, solutions, water-soluble powders and water-soluble granules, followed by blending these formulations at appropriate ratios; or formulated by mixing all of the active ingredients at once with conventional solid or liquid carriers, surfactants and other adjuvants to form conventional formulations such as wettable powders, flowables and water-dispersible glanules.

These formulations contain the active ingredients (a) and (b) at a total content of from 1% to 90% by weight, preferably from 2% to 80% by weight.

Examples of the solid carrier are fine powders or granules of kaolin clay, attapulgite clay, bentonite, terra alba, pyrophyllite, talc, diatomaceous earth, calcite, walnut shell powders, urea, ammonium sulfate and synthetic hydrated silica. As the liquid carrier, used are aromatic hydrocarbons such as xylene and methylnaphthalene; alcohols such as isopropanol, ethylene glycol and cellosolve; ketones such as acetone, cyclohexanone and isophorone; vegetable oils such as soybean oil and cotton seed oil; dimethylsulfoxide, N,N-dimethylformamide, acetonitrile, water or the like.

Examples of the surfactant used for emulsification, dispersing or spreading are those of anionic type, such as alkylsulfates, alkylsulfonates, alkylarylsulfonates, dialkylsulfosuccinates (salts or esters) and phosphates of polyoxyethylene alkylaryl ethers; and those of nonionic type, such as polyoxyethylene alkyl ethers, polyoxyethylene alkylaryl ethers, polyoxyethylene polyoxypropylene block copolymers, sorbitan fatty acid esters and polyoxyethylene sorbitan fatty acid esters.

Examples of the auxiliary agent are ligninsulfonates, alginates, polyvinyl alcohol, gum arabic, carboxymethyl cellulose (CMC) and isopropyl acid phosphate (PAP).

The herbicidal composition of the present invention can be used as a herbicide to be employed for upland fields, non-cropping fields, levees of paddy fields, orchards, pusturelands, lawns, forests or non-agricultural fields. The herbicidal composition of the present invention is used for post-emergence control of undesired weeds by foliar treatment.

The dosage of the herbicidal composition of the present invention may vary depending upon the mixing ratio of active ingredients, formulation type employed, species of undesired weeds to be controlled, prevailing weather conditions and the like. Usually, however, the total amount of the active ingredients to be applied is from 100 to 5000 grams, preferably from 200 to 3000 grams per hectare. The herbicidal composition formulated in any suitable formulation may usually be employed by diluting it with water at a volume of from about 100 to 1000 liters per hectare, if necessary, with addition of an adjuvant such as a spreading agent. Examples of the adjuvant are, in addition to the surfactants as described above, polyoxyethylene resin acids (esters), ligninsulfonates, abietates, dinaphthylmethanedisulfonates, petroleum oil, crop oil concentrate and crop oil such as soybean oil, corn oil, cotton seed oil and sunflower oil.

Further, the herbicidal composition of the present invention may be used together with any other herbicide to enhance its herbicidal activity, and in some cases, synergistic effects can be expected. Moreover, it may also be used in admixture with insecticides, acaricides, nematocides, fungicides, plant growth regulators, fertilizers and the like.

The present invention will be explained in more detail by way of the following Formulation Examples and Test Examples, which are not to be construed to limit the scope thereof.

The following will describe Formulation Examples of the active ingredient (a), wherein all parts are by weight.

Formulation Example 1

Eighty parts of ingredient (a), 5 parts of polyoxyethylene alkylaryl ether and 15 parts of synthetic hydrated silica are well mixed while being powdered to obtain a wettable powder.

Formulation Example 2

Ten parts of ingredient (a), 7 parts of polyoxyethylene alkylaryl ether, 3 parts of alkylarylsulfonate and 80 parts of cyclohexanone are well mixed to obtain an emulsifiable concentrate.

Formulation Example 3

Twenty parts of ingredient (a) are mixed with 60 parts of water containing 3% by weight of polyoxyethylene sorbitan monooleate, and the mixture is pulverized until the particle size becomes less than 3 microns, after which 20 parts of an aqueous solution containing 3% by weight of sodium alginate are added to obtain a flowable.

The practical herbicidal activity and phytotoxicity of the herbicidal composition of the present invention will be described with reference to the following Test Examples, wherein they are shown by a rating of from 0 (no influence) to 10 (complete dying). The glyphosate, bialaphos and glufosinate used in these Test Examples refer to the commercially available herbicide named "Roundup®" (containing 41% by weight of glyphosate as an isopropylamine salt), commercially available herbicide named "Herbiace®" (aqueous solution containing 20% by weight of bialaphos as a sodium salt) and commercially available herbicide named "Basta®" (liquid formulation containing 18.5% by weight of glufosinate as an ammonium salt), respectively.

Test Example 1

Plastic vats (area, 17×25 cm$^2$; depth, 7 cm) were filled with upland field soil, and the seeds of corn spurry (*Spergula arvensis*) as a test plant were sowed therein, followed by cultivation of the test plant in a greenhouse for 20 days. The active ingredient (a) formulated in an emulsifiable concentrate as in Formulation Example 2 and glyphosate as the active ingredient (b) at the designated amounts were diluted with water. The dilution was uniformly sprayed over the foliage of the test plant by means of a small sprayer at a spray volume of 1000 liters per hectare. At that time, the test plant was from 6 to 8 cm in height. Thereafter, the test plant was further grown in the greenhouse for 3 days, and the herbicidal activity was examined. The results are shown in Table 1.

TABLE 1

| Active ingredient | Dosage (g/ha) | Herbicidal activity |
| --- | --- | --- |
| (a) only | 10 | 3.0 |
|  | 100 | 3.9 |
| (b) only | 600 | 1.2 |
|  | 2000 | 1.9 |
| (a) + (b) | 10 + 600 | 8.0 |
|  | 100 + 2000 | 8.9 |

Test Example 2

Plastic vats (area, 17×25 cm$^2$; depth, 7 cm) were filled with upland field soil, and the seeds of common purslane (*Portulaca oleracea*) as a test plant were sowed therein, followed by cultivation of the test plant in a greenhouse for 27 days. The active ingredient (a) formulated in a wettable powder as in Formulation Example 1 and glyphosate as the active ingredient (b) at the designated amounts were diluted with water containing a 0.2% (v/v) spreading agent (containing an 80% polyoxyethylene dodecyl ether type surfactant). The dilution was uniformly sprayed over the foliage of the test plant by means of a small sprayer at a spray volume of 1000 liters per hectare. At that time, the test plant was from 25 to 30 cm in height. Thereafter, the test plant was further grown in the greenhouse for 29 days. The herbicidal activity was examined 3 days and 29 days after the treatment. The results are shown in Table 2.

TABLE 2

| Active ingredient | Dosage (g/ha) | Herbicidal activity | |
| --- | --- | --- | --- |
|  |  | 3 DAT* | 29 DAT* |
| (a) only | 50 | 6.5 | 9.0 |
|  | 100 | 8.0 | 9.5 |
|  | 200 | 9.0 | 10.0 |
| (b) only | 600 | 0.5 | 7.0 |
|  | 1200 | 0.5 | 9.5 |
| (a) + (b) | 50 + 600 | 8.0 | 10.0 |
|  | 50 + 1200 | 9.5 | 10.0 |
|  | 100 + 600 | 9.0 | 10.0 |

TABLE 2-continued

| Active ingredient | Dosage (g/ha) | Herbicidal activity | |
| --- | --- | --- | --- |
|  |  | 3 DAT* | 29 DAT* |
|  | 100 + 1200 | 9.5 | 10.0 |
|  | 200 + 600 | 10.0 | 10.0 |
|  | 200 + 1200 | 10.0 | 10.0 |

*DAT: Days after treatment

Test Example 3

Plastic vats (area, 17×25 cm$^2$; depth, 7 cm) were filled with upland field soil, and the seeds of large crabgrass (*Digitaria sanguinalis* as a test plant were sowed therein, followed by cultivation of the test plant in a greenhouse for 27 days. The active ingredient (a) formulated in a wettable powder as in Formulation Example 1 and glyphosate as the active ingredient (b) at the designated amounts were diluted with water containing a 0.2% (v/v) spreading agent (containing an 80% polyoxyethylene dodecyl ether type surfactant). The dilution was uniformly sprayed over the foliage of the test plant by means of a small sprayer at a spray volume of 1000 liters per hectare. At that time, the test plant was from 15 to 20 cm in height. Thereafter, the test plant was further grown in the greenhouse for 29 days. The herbicidal activity was examined 3 days and 29 days after the treatment. The results are shown in Table 3.

TABLE 3

| Active ingredient | Dosage (g/ha) | Herbicidal activity | |
| --- | --- | --- | --- |
|  |  | 3 DAT | 29 DAT |
| (a) only | 50 | 2.0 | 2.5 |
|  | 100 | 3.0 | 4.0 |
|  | 200 | 3.5 | 5.0 |
| (b) only | 800 | 2.5 | 9.0 |
|  | 1200 | 3.0 | 9.5 |
| (a) + (b) | 50 + 800 | 8.0 | 10.0 |
|  | 50 + 1200 | 8.5 | 10.0 |
|  | 100 + 800 | 8.5 | 10.0 |
|  | 100 + 1200 | 9.0 | 10.0 |
|  | 200 + 800 | 8.5 | 10.0 |
|  | 200 + 1200 | 9.0 | 10.0 |

Test Example 4

Plastic vats (area, 17×25 cm$^2$; depth, 7 cm) were filled with upland field soil, and the seeds of large crabgrass (*Digitaria sanquinalis*) as a test plant were sowed therein, followed by cultivation of the test plant in a greenhouse for 27 days. The active ingredient (a) formulated in a wettable powder as in Formulation Example 1 and glufosinate as the active ingredient (b) at the designated amounts were diluted with water containing a 0.2% (v/v) spreading agent (containing an 80% polyoxyethylene dodecyl ether type surfactant). The dilution was uniformly sprayed over the foliage of the test plant by mean of a small sprayer at a spray volume of 1000 liters per hectare. At that time, the test plant was from 15 to 20 cm in height. Thereafter, the test plant was further grown in the greenhouse for 28 days. The herbicidal activity was examined 2 days and 28 days after the treatment. The results are shown in Table 4.

TABLE 4

| Active ingredient | Dosage (g/ha) | Herbicidal activity 2 DAT | Herbicidal activity 28 DAT |
| --- | --- | --- | --- |
| (a) only | 50 | 2.0 | 2.5 |
|  | 100 | 2.5 | 4.0 |
|  | 200 | 3.5 | 5.0 |
| (b) only | 500 | 4.0 | 9.5 |
|  | 650 | 4.5 | 10.0 |
|  | 800 | 5.0 | 10.0 |
| (a) + (b) | 50 + 500 | 8.0 | 10.0 |
|  | 50 + 650 | 8.5 | 10.0 |
|  | 50 + 800 | 9.0 | 10.0 |
|  | 100 + 500 | 8.5 | 10.0 |
|  | 100 + 650 | 8.5 | 10.0 |
|  | 100 + 800 | 9.0 | 10.0 |
|  | 200 + 500 | 9.0 | 10.0 |
|  | 200 + 650 | 9.0 | 10.0 |
|  | 200 + 800 | 9.5 | 10.0 |

Test Example 5

Plastic vats (area, 17×25 cm²; depth, 7 cm) were filled with upland field soil, and the seeds of giant foxtail (*Setaria faberi*) as a test plant were sowed therein, followed by cultivation of the test plant outdoors for 25 days. The active ingredient (a) formulated in a wettable powder as in Formulation Example 1 and bialaphos as the active ingredient (b) at the designated amounts were diluted with water containing a 0.2% (v/v) spreading agent (containing an 80% polyoxyethylene dodecyl ether type surfactant). The dilution was uniformly sprayed over the foliage of the test plant by means of a small sprayer at a spray volume of 1000 liters per hectare. At that time, the test plant was from 20 to 25 cm in height. Thereafter, the test plant was further grown outdoors for 35 days. The herbicidal activity was examined 4 days and 35 days after the treatment. The results are shown in Table 5.

TABLE 5

| Active ingredient | Dosage (g/ha) | Herbicidal activity 4 DAT | Herbicidal activity 35 DAT |
| --- | --- | --- | --- |
| (a) only | 50 | 1.0 | 1.5 |
|  | 200 | 2.5 | 3.0 |
| (b) only | 600 | 5.5 | 6.5 |
|  | 1200 | 6.5 | 10.0 |
| (a) + (b) | 50 + 600 | 7.5 | 10.0 |
|  | 50 + 1200 | 8.5 | 10.0 |
|  | 200 + 600 | 9.0 | 10.0 |
|  | 200 + 1200 | 9.5 | 10.0 |

Test Example 6

Plastic vats (area, 17×25 cm²; depth, 7 cm) were filled with upland field soil. The active ingredient (a) formulated in a wettable powder as in Formulation Example 1 and glyphosate, bialaphos or glufosinate as the active ingredient (b) at the designated amounts were diluted with water containing a 0.2% (v/v) spreading agent (containing an 80% polyoxyethylene dodecyl ether type surfactant). The dilution was uniformly sprayed on the soil surface by mean of a small sprayer at a spray volume of 1000 liters per hectare. After 6 days, the surface soil about 2 cm in depth was uniformly mixed, and the seeds of radish (*Raphanus sativus*), onion (*Allium cepa*) and carrot (*Daucus carota* var. *sativus*) as test plants were sowed therein in 1 cm depth. Thereafter, the test plants were cultivated in a greenhouse for 33 days, and the phytotoxicity against the respective test plants was examined. The results are shown in Table 6.

TABLE 6

| Active ingredient | Dosage (g/ha) | Phytotoxicity Radish | Phytotoxicity Onion | Phytotoxicity Carrot |
| --- | --- | --- | --- | --- |
| (a) + Glyphosate | 400 + 1200 | 0 | 0 | 0 |
| (a) + Glufosinate | 400 + 800 | 0 | 0 | 0 |
| (a) + Bialaphos | 400 + 1200 | 0 | 0 | 0 |

What is claimed is:

1. A herbicidal composition comprising of (a) 2-[4-chloro-2-fluoro-5-(n-pentyloxycarbonylmethoxy)phenyl]-4,5,6,7-tetrahydro-2H-isoindole-1,3-dione and (b) at least one selected from the group consisting of N-(phosphonomethyl)glycine, (2-amino-4-methylphosphinobutyryl)alanylalanine, DL-homoalanin-4-yl(methyl)phosphinic acid and salts thereof.

2. A composition according to claim 1, wherein the weight ratio of ingredients (a) to (b) is 1:0.25 to 100.

3. A composition according to claim 1, wherein the weight ratio of ingredients (a) to (b) is 1:0.5 to 70.

4. A composition according to claim 1, wherein said ingredient (b) is selected from N-(phosphonomethyl)glycine and salts thereof.

5. A composition according to claim 4, wherein the weight ratio of ingredients (a) to (b) is 1:0.25 to 100.

6. A composition according to claim 4, wherein the weight ratio of ingredients (a) to (b) is 1:0.5 to 70.

7. A composition according to claim 1, wherein said ingredient (b) is selected from (2-amino-4-methylphosphinobutyryl)alanylalanine and salts thereof.

8. A composition according to claim 7, wherein the weight ratio of ingredients (a) to (b) is 1:0.25 to 100.

9. A composition according to claim 7, wherein the weight ratio of ingredients (a) to (b) is 1:0.5 to 70.

10. A composition according to claim 1, wherein said ingredient (b) is selected from DL-homoalanin-4-yl(methyl)phosphinic acid and salts thereof.

11. A composition according to claim 10, wherein the weight ratio of ingredients (a) to (b) is 1:0.25 to 100.

12. A composition according to claim 10, wherein the weight ratio of ingredients (a) to (b) is 1:0.5 to 70.

13. A method for controlling undesired weeds, which comprises applying a herbicidally effective amount of the herbicidal composition according to claim 1 to the area where undesired weeds grow.

14. A method according to claim 13, wherein the total amount of ingredients (a) and (b) in the composition is from 100 to 5000 grams per hectare.

15. A method according to claim 13, wherein the total amount of ingredients (a) and (b) in the composition is from 200 to 3000 grams per hectare.

16. A method according to claim 13, wherein said ingredient (b) is selected from N-(phosphonomethyl)glycine and salts thereof.

17. A method according to claim 16, wherein the total amount of ingredients (a) and (b) in the composition is from 100 to 5000 grams per hectare.

18. A method according to claim 16, wherein the total amount of ingredients (a) and (b) in the composition is from 200 to 3000 grams per hectare.

19. A method according to claim 13, wherein said ingredient (b) is selected from (2-amino-4-methylphosphinobutyryl)alanylalanine and salts thereof.

20. A method according to claim 19, wherein the total amount of ingredients (a) and (b) in the composition is from 100 to 5000 grams per hectare.

21. A method according to claim 19, wherein the total amount of ingredients (a) and (b) in the composition is from 200 to 3000 grams per hectare.

22. A method according to claim 13, wherein said ingredient (b) is selected from DL-homoalanin-4-yl(methyl)phosphinic acid and salts thereof.

23. A method according to claim 22, wherein the total amount of ingredients (a) and (b) in the composition is from 100 to 5000 grams per hectare.

24. A method according to claim 22, wherein the total amount of ingredients (a) and (b) in the composition is from 200 to 3000 grams per hectare.

* * * * *